(12) United States Patent
Koishi

(10) Patent No.: US 8,917,928 B2
(45) Date of Patent: Dec. 23, 2014

(54) SYSTEM AND METHOD FOR RADIOGRAPHING INFORMATION MANAGEMENT AND RECORDING MEDIUM STORING PROGRAM THEREFOR

(71) Applicant: FUJIFILM Corporation, Tokyo (JP)

(72) Inventor: Takeshi Koishi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 147 days.

(21) Appl. No.: 13/774,127

(22) Filed: Feb. 22, 2013

(65) Prior Publication Data

US 2013/0251232 A1   Sep. 26, 2013

(30) Foreign Application Priority Data

Mar. 22, 2012 (JP) ................................. 2012-065552

(51) Int. Cl.
*G06K 9/00* (2006.01)
*G06T 7/00* (2006.01)
*G06F 19/00* (2011.01)
*A61B 6/00* (2006.01)

(52) U.S. Cl.
CPC .......... *G06T 7/0014* (2013.01); *G06F 19/3481* (2013.01); *A61B 6/4494* (2013.01); *G06F 19/327* (2013.01); *A61B 6/563* (2013.01)
USPC ............. 382/132; 382/131; 378/62; 378/108; 600/1

(58) Field of Classification Search
USPC ............. 382/131, 132; 378/62, 108; 705/2, 3; 600/1
See application file for complete search history.

(56) References Cited

U.S. PATENT DOCUMENTS

| | | | | |
|---|---|---|---|---|
| 7,611,452 B2 * | 11/2009 | Allison et al. | ..................... | 600/1 |
| 7,831,289 B2 * | 11/2010 | Riker et al. | ................... | 600/407 |
| 7,949,098 B2 * | 5/2011 | Ellinwood et al. | ............ | 378/108 |
| 8,095,384 B2 * | 1/2012 | Firminger et al. | ................ | 705/2 |
| 2005/0209888 A1 | 9/2005 | Oowaki et al. | | |
| 2013/0051704 A1 * | 2/2013 | Koishi | .......................... | 382/305 |
| 2013/0085780 A1 * | 4/2013 | Braunstein et al. | ............... | 705/3 |
| 2014/0161339 A1 * | 6/2014 | Wakai | ........................... | 382/131 |

FOREIGN PATENT DOCUMENTS

JP     2006-150033 A    6/2006

* cited by examiner

*Primary Examiner* — Katrina Fujita
(74) *Attorney, Agent, or Firm* — Birch, Stewart, Kolasch & Birch, LLP

(57) ABSTRACT

A search processing unit of a central server searches for radiographing information matched with a designated radiographing part, among all items of the radiographing information of a medical facility having radiographing information matched with a detection device ID from a storage device. A sorting unit performs classification into medical facilities (first group), in which the radiation dose after an X-ray image detection device of the designated detection device ID is introduced has changed from that before the introduction, and medical facilities (second group) in which the radiation dose after the X-ray image detection device of the designated detection device ID is introduced has not changed. A statistical data generation unit generates a histogram, in which the range of radiation dose is set as the class on the horizontal axis and the number of medical facilities is set as the frequency on the vertical, for each of first and second groups.

13 Claims, 14 Drawing Sheets

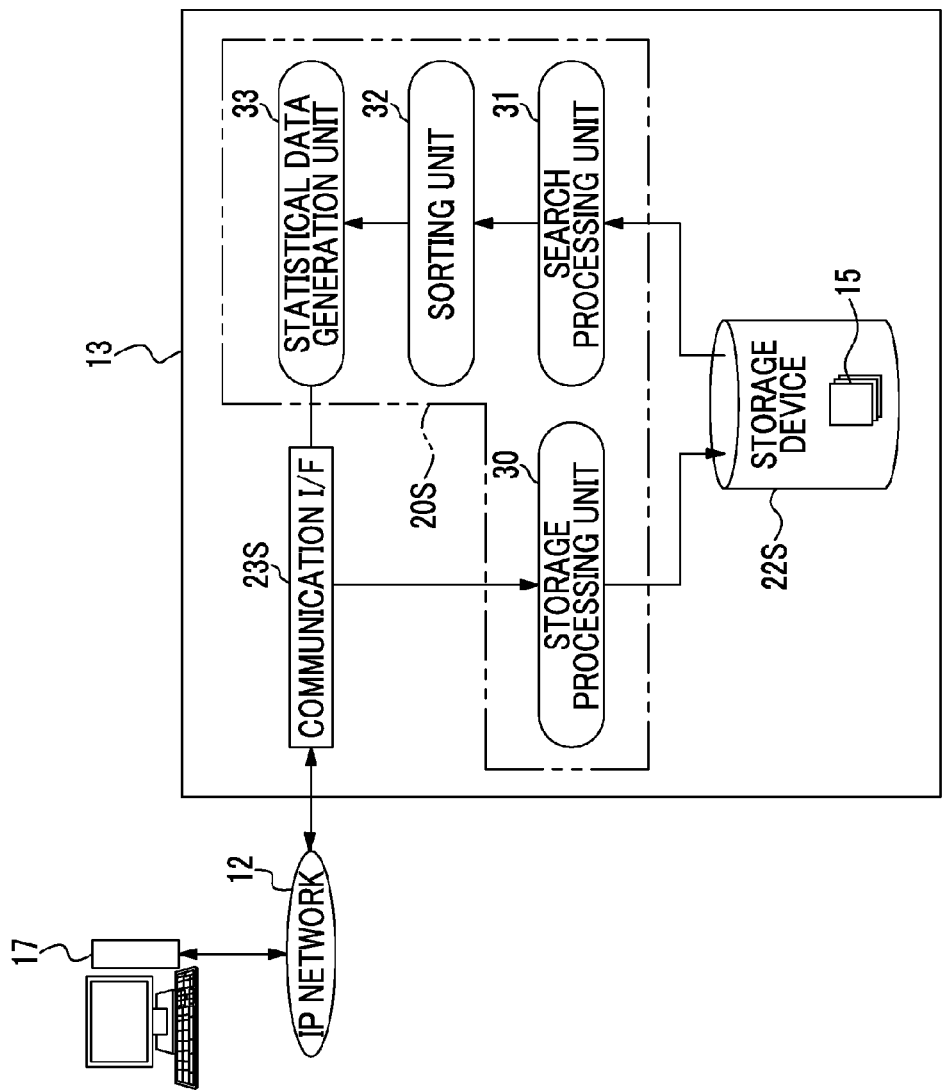

FIG. 5B

RADIOGRAPHING INFORMATION LIST OF MEDICAL FACILITY B
(RADIOGRAPHING PART: CHEST)

| DETECTION DEVICE ID | RADIOGRAPHING DATE AND TIME | RADIATION DOSE |
|---|---|---|
| ... | ... | ... |
| D0072 | 12-16-2011 15:14 | 65.0 μSv |
| D0072 | 12-16-2011 15:58 | 65.0 μSv |
| D0072 | 02-29-2012 14:08 | 65.0 μSv |
| D0088 | 02-29-2012 16:22 | 65.0 μSv |
| D0088 | 03-31-2012 10:15 | 65.0 μSv |
| ... | ... | ... |
| D0090 | 04-12-2014 11:17 | 65.0 μSv |
| ... | ... | ... |

BEFORE INTRODUCTION ↔ AFTER INTRODUCTION

NOT CHANGED → CLASSIFIED INTO SECOND GROUP

HISTOGRAM OF FIRST GROUP (FIRST STATISTICAL DATA)

HISTOGRAM OF SECOND GROUP (SECOND STATISTICAL DATA)

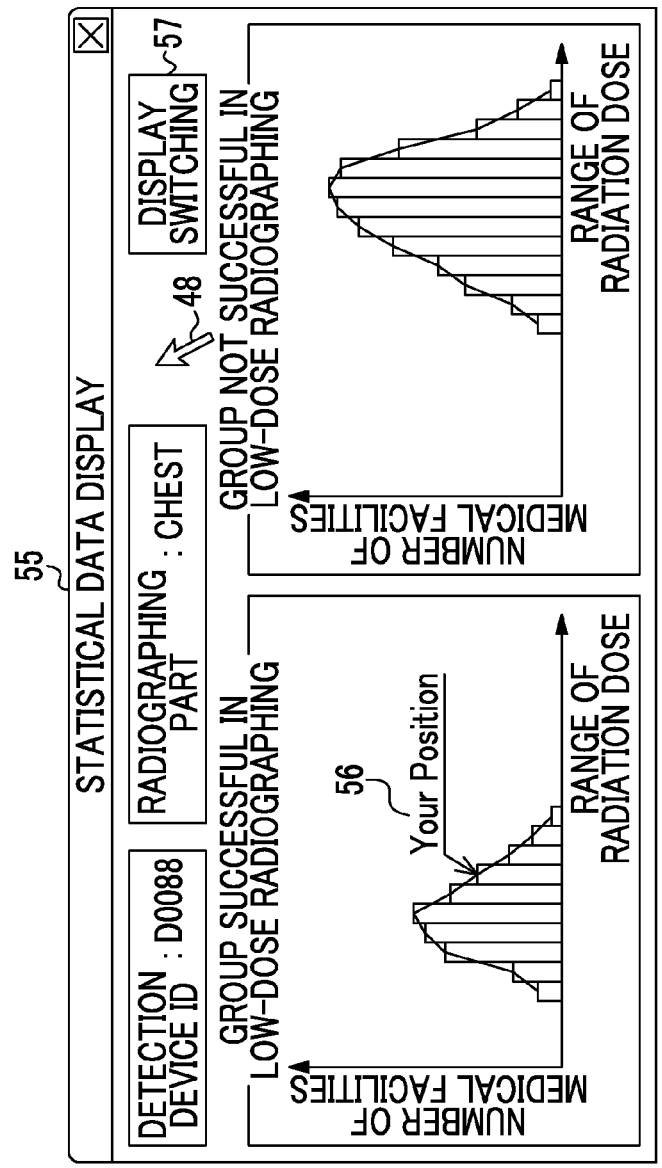

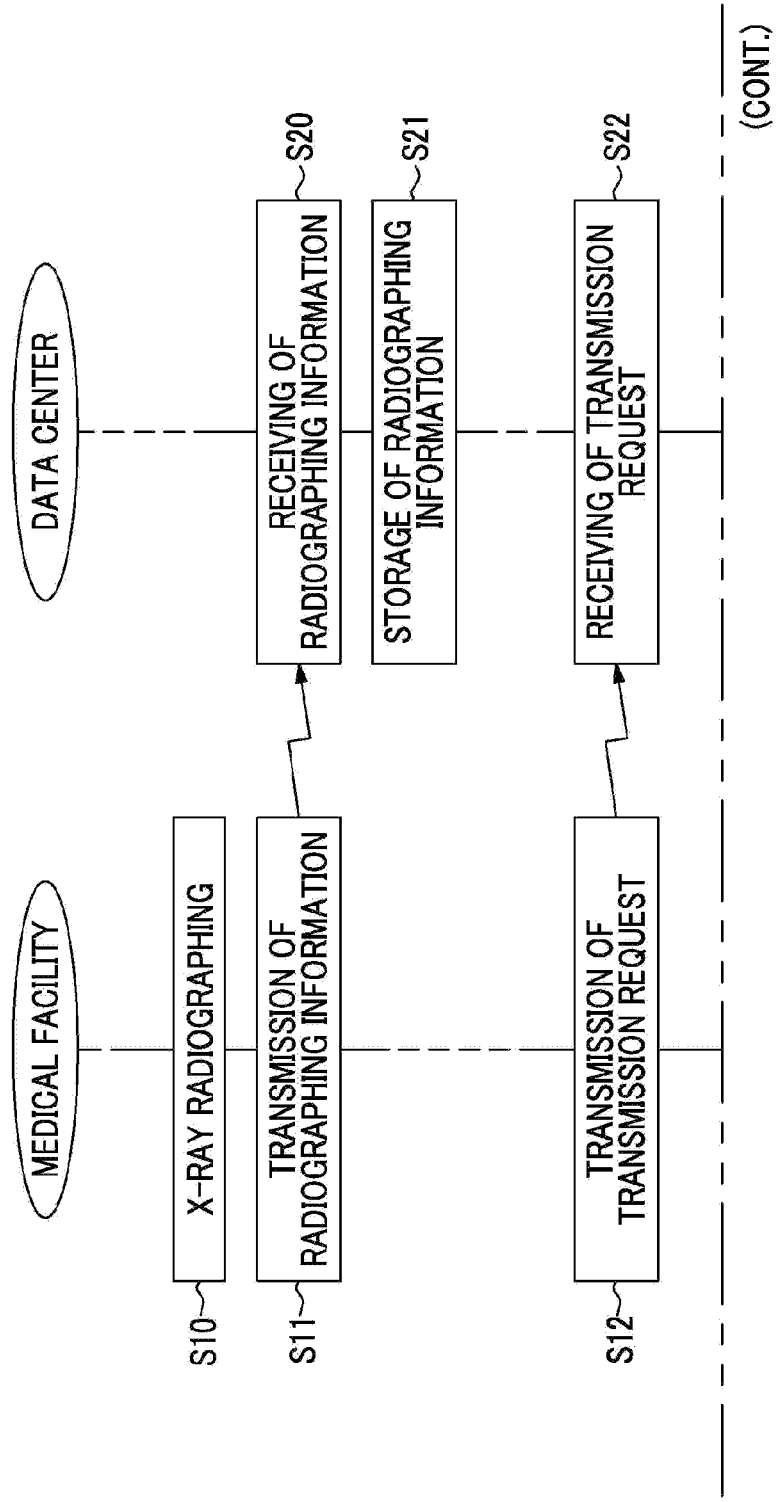

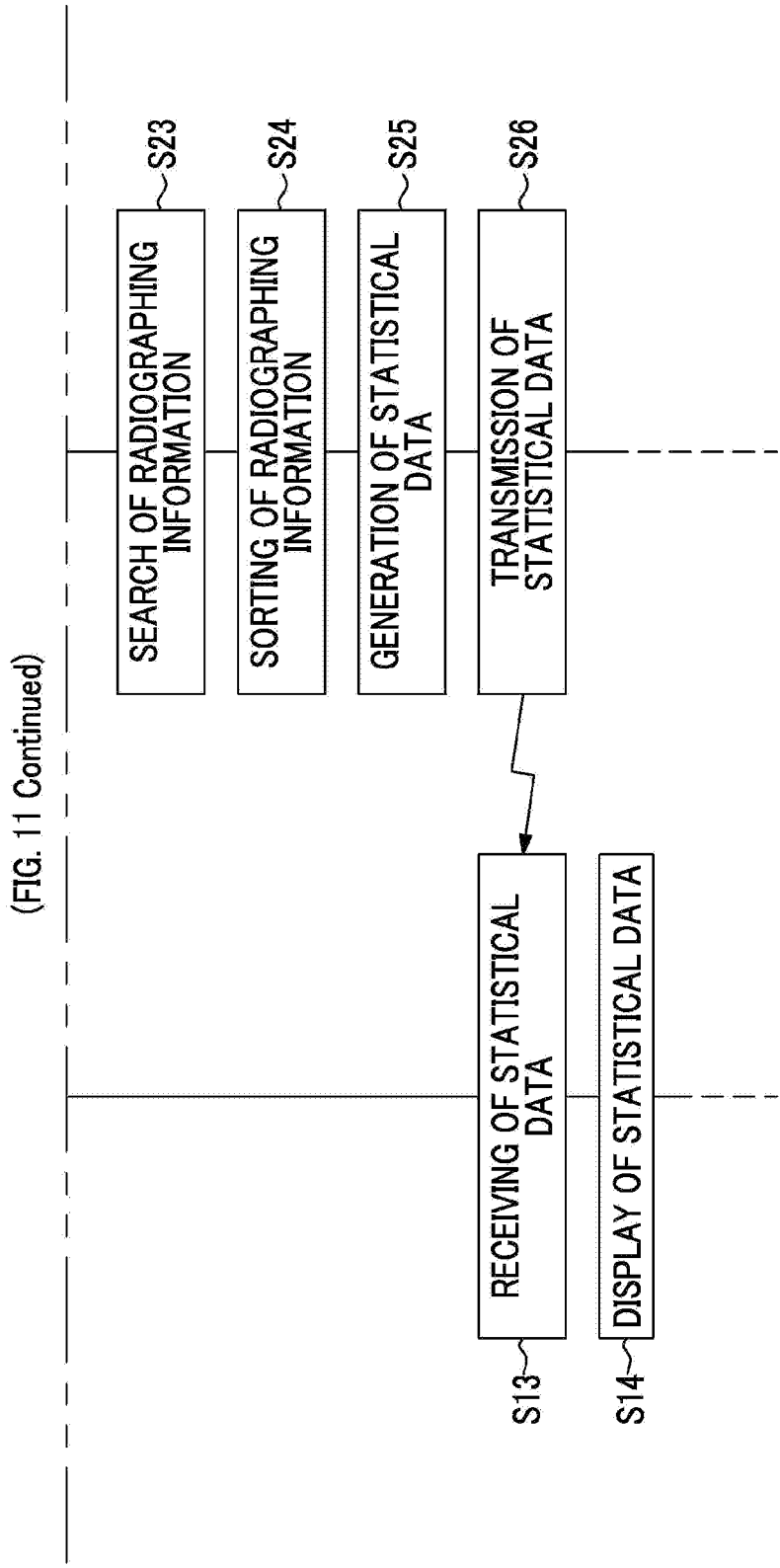

SYSTEM AND METHOD FOR RADIOGRAPHING INFORMATION MANAGEMENT AND RECORDING MEDIUM STORING PROGRAM THEREFOR

BACKGROUND OF THE INVENTION

1. Field of the Invention

The present invention relates to a system and method for radiographing information management, which manages radiographing information and provides support services for low-dose radiographing, and a program therefor.

2. Description of the Related Art

In the medical field, X-ray radiographing systems using radiation, for example, X-rays are known. In the field of recent X-ray radiographing systems, an X-ray image detection device that uses a flat panel detector (FPD) as a detection panel instead of an X-ray film or an imaging plate (IP) has become widespread. An electronic cassette (portable X-ray image detection device) in which an FPD is built into the housing having a rectangular parallelepiped shape has already been put to practical use.

The sensitivity of the X-ray image detection device has improved with the development of such a detection panel. As a result, the same X-ray image as in the related art or a clearer image than in the related art can be obtained with a low radiation dose. In addition, with a recent trend of reducing the dose of exposure to the patient and an increase in the sensitivity of the X-ray image detection device, medical facilities are also required to perform radiographing with a radiation dose as low as possible.

JP2006-150033A discloses a system that stores and manages dose information, which is transmitted from X-ray radiographing systems of a plurality of medical facilities or radiographing rooms, in time series and provides various kinds of information that may be of assistance to low-dose radiographing. As search and classification conditions of the dose information, the type of an X-ray image detection device can be designated. This system generates a histogram, in which the vertical axis indicates the number of medical facilities and the horizontal axis indicates the radiation dose, based on the searched information and provides the histogram to the client. By viewing the histogram, the client can check how much radiation dose is used to perform radiographing in the medical facility where the type of the X-ray image detection device is used.

SUMMARY OF THE INVENTION

When a new X-ray image detection device is introduced, there are medical facilities, in which the radiation dose from the X-ray source is reset to the optimal value corresponding to the X-ray image detection device, and medical facilities, in which the radiation dose of the old device that has been used in the past is used as it is without resetting the radiation dose. In the latter case, even if a new X-ray image detection device with high sensitivity is introduced with difficulty, there is no change in the radiation dose after the introduction from that before. Presumably, the reason why such a thing occurs even though low-dose radiographing can be realized is that it is difficult to determine which level of low-dose radiographing can be specifically realized quantitatively and visually when a certain type of X-ray image detection device is introduced.

In the invention disclosed in JP2006-150033A, dose information is searched for in a state where the type of an X-ray image detection device is designated, and the histogram is provided based on the searched information. However, a client who optimizes the radiation dose in order to realize low-dose radiographing after introducing the type of X-ray image detection device and a client who does not optimize the radiation dose are not distinguished from each other. For this reason, even if the radiation dose is visualized using a histogram, the optimal radiation dose cannot be determined quantitatively or visually.

The present invention has been made in view of the above problems and an object of the present invention is to provide a system and method for radiographing information management, which can generate useful material for the realization of low-dose radiographing, and a non-transitory computer-readable recording medium that records a program.

In order to achieve the above-described object, according to an aspect of the present invention, there is provided a radiographing information management system including: a storage processing unit that stores radiographing information in a storage unit; a search unit that searches for desired radiographing information from the storage unit; an analysis unit that analyzes the radiographing information; and a statistical data generation unit that generates statistical data based on the radiographing information analyzed by the analysis unit. The radiographing information includes at least source identification information indicating a source of the radiographing information, detection device identification information indicating a radiological image detection device used in radiographing, and information regarding a radiation dose. The search unit searches for, from the radiographing information, radiographing information when performing radiographing using a designated radiological image detection device. The analysis unit groups the radiographing information for each item of the source identification information, assesses states before and after introduction of the radiological image detection device based on detection device identification information or information regarding switching of a type of a radiological image detection device among the grouped radiographing information items, and performs classification into a first group in which a difference between information regarding a radiation dose before the radiological image detection device is introduced and information regarding a radiation dose after the radiological image detection device is introduced exceeds a predetermined range and a second group in which the difference falls within the predetermined range. The statistical data generation unit generates statistical data of at least the first group.

Preferably, a display unit that displays statistical data generated by the statistical data generation unit is further included. When the statistical data generation unit generates statistical data of the first and second groups, the display unit displays the statistical data of the first and second groups so as to be compared with each other or displays only the statistical data of the first group.

The statistical data generation unit generates a histogram, in which a vertical axis indicates the number of groups and a horizontal axis indicates a range of a radiation dose or an equivalent amount equivalent to the radiation dose, as statistical data.

The statistical data generation unit calculates optimal radiographing conditions from the statistical data of the first group. An example of the optimal radiographing conditions is the average of the radiographing conditions of the first group.

The search unit performs searching in response to a transmission request of statistical data including detection device identification information to be searched for. The radiographing information includes information of a radiographing part, and the transmission request includes information of a radiographing part. The search unit searches for radiographing information, which is matched with a radiographing part designated in the transmission request, among radiographing information having detection device identification information designated in the transmission request.

The analysis unit excludes a group of radiographing information, for which a predetermined period has not passed since the radiological image detection device has been introduced, from objects to be classified.

The radiographing information includes, as the source identification information, any one of a medical facility in which a radiographing system is placed, a radiographer in charge of radiographing, and a radiographing room where radiographing is performed, and the analysis unit groups radiographing information based on any one of the medical facility, the radiographer, and the radiographing room. In addition, the grouping may be performed after the searching of the search unit, or may be performed when storing the radiographing information in the storage unit.

Information regarding the switching of a type of the radiological image detection device is date and time when the radiological image detection device is newly introduced.

The information regarding the radiation dose is any one of the radiation dose itself, a tube current irradiation time product, and a reading sensitivity value obtained by histogram analyzing of a radiological image.

According to another aspect of the present invention, there is provided a radiographing information management method including: a storage processing step of storing radiographing information in a storage unit using a storage processing unit; a search step of searching for desired radiographing information from the storage unit using a search unit; an analysis step of analyzing the radiographing information; and a statistical data generation step of generating statistical data based on the radiographing information analyzed in the analysis step using a statistical data generation unit. The radiographing information includes at least source identification information indicating a source of the radiographing information, detection device identification information indicating a radiological image detection device used in radiographing, and information regarding a radiation dose. In the search step, radiographing information when performing radiographing using a designated radiological image detection device is searched for from the radiographing information. In the analysis step, the radiographing information is grouped for each item of the source identification information, states before and after introduction of the radiological image detection device are assessed based on detection device identification information or information regarding switching of a type of a radiological image detection device among the grouped radiographing information items, and classification into a first group in which a difference between information regarding a radiation dose before the radiological image detection device is introduced and information regarding a radiation dose after the radiological image detection device is introduced exceeds a predetermined range and a second group in which the difference falls within the predetermined range is performed. In the statistical data generation step, statistical data of at least the first group is generated.

According to still another aspect of the present invention, there is provided a non-transitory computer-readable recording medium that records a radiographing information management program causing a computer to realize: a storage processing function of storing radiographing information in a storage unit; a search function of searching for desired radiographing information from the storage unit; an analysis function of analyzing the radiographing information; and a statistical data generation function of generating statistical data based on the radiographing information analyzed by the analysis function. The radiographing information includes at least source identification information indicating a source of the radiographing information, detection device identification information indicating a radiological image detection device used in radiographing, and information regarding a radiation dose. Using the search function, radiographing information when performing radiographing using a designated radiological image detection device is searched for from the radiographing information. Using the analysis function, the radiographing information is grouped for each item of the source identification information, states before and after introduction of the radiological image detection device are assessed based on detection device identification information or information regarding switching of a type of a radiological image detection device among the grouped radiographing information items, and classification into a first group in which a difference between information regarding a radiation dose before the radiological image detection device is introduced and information regarding a radiation dose after the radiological image detection device is introduced exceeds a predetermined range and a second group in which the difference falls within the predetermined range is performed. Using the statistical data generation function, statistical data of at least the first group is generated.

According to the aspect of the present invention, after a certain type of radiological image detection device is introduced, classification into the first group, in which a change in the radiation dose or the equivalent amount in the radiographing information of the radiological image detection device after the radiological image detection device is introduced exceeds a predetermined range, and the second group, in which the changes falls within the predetermined range, is performed, and statistical data is generated for at least the first group. Therefore, useful material for realizing low-dose radiographing can be generated.

BRIEF DESCRIPTION OF THE DRAWINGS

FIG. 4 is a block diagram showing the internal configuration of a central server.

FIGS. 5A and 5B are diagrams showing states where the radiographing information designated in a transmission request is listed by a sorting unit.

FIG. 10 is a diagram showing a statistical data display window.

FIG. 11 is a flow chart showing the flow of the process of the X-ray radiographing information management system.

DESCRIPTION OF THE PREFERRED EMBODIMENTS

Figure 1:
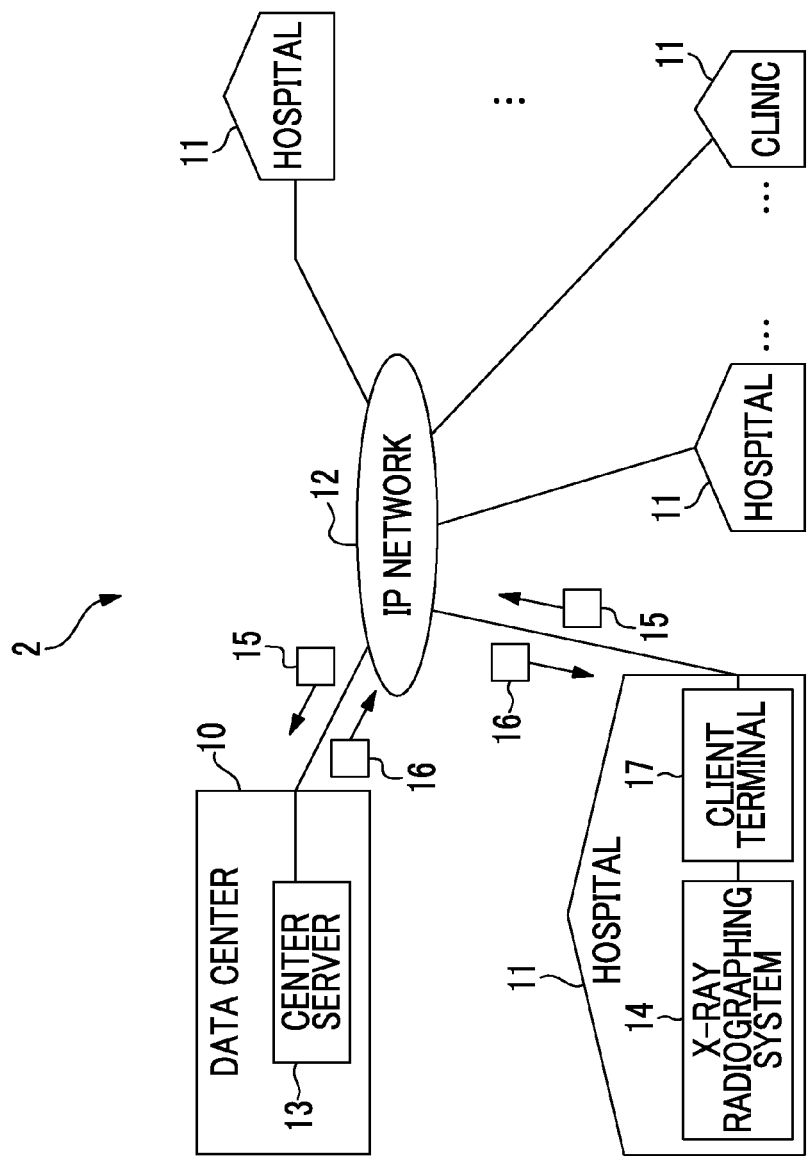
FIG. 1 is a schematic diagram showing the configuration of an X-ray radiographing information management system.

In FIG. 1, an X-ray radiographing information management system 2 is configured to include a data center 10 and a plurality of medical facilities 11. The data center 10 and each of the medical facilities 11 are connected to each other through an IP network 12. Since a dedicated wide area IP network owned by the communication service provider is used as a base network, the IP network 12 is a closed network obtained by constructing a VPN (Virtual Private Network) on the wide area IP network. Due to the VPN, information transmitted through the IP network 12 does not leak to the outside of the X-ray radiographing information management system 2, and the security of information is ensured.

A central server 13 is provided in the data center 10. The central server 13 stores and manages radiographing information 15 of an X-ray radiographing system 14 placed in each medical facility 11, generates statistical data 16 based on the radiographing information 15, and distributes the statistical data 16 to each of the medical facilities 11 to provide support services for low-dose radiographing to each medical facility 11.

The medical facilities 11 include relatively large hospitals, such as university hospitals, and relatively small hospitals, such as privately owned clinics. The X-ray radiographing system 14 and a client terminal 17 are placed in each medical facility 11. The X-ray radiographing system 14 and the client terminal 17 (an aspect of a display unit) are connected to each other through a LAN placed in the medical facility 11 (refer to FIG. 12).

The X-ray radiographing system 14 has a known configuration including an X-ray source that emits X-rays, an X-ray image detection device that detects X-rays transmitted through a subject and outputs an X-ray image, a control device that controls their operations, a standing radiography platform, and a recumbent radiography platform. In addition, the X-ray radiographing system 14 has a dose detection sensor that detects the dose of irradiated X-rays.

The client terminal 17 transmits (uploads) the radiographing information 15 of the X-ray radiographing system 14 to the central server 13 and also receives (downloads) the statistical data 16 from the central server 13. The radiographing information 15 may be transmitted each time the radiographing is performed by the X-ray radiographing system 14, or the radiographing information 15 of a predetermined period, such as one day or one week, may be stored in the client terminal 17 and may be collectively transmitted. Alternatively, a cyclic monitoring function may be set in the central server 13, so that the central server 13 checks that the radiographing information 15 has been uploaded to the client terminal 17 and the radiographing information 15 is automatically transmitted by the client terminal 17.

Figure 2:
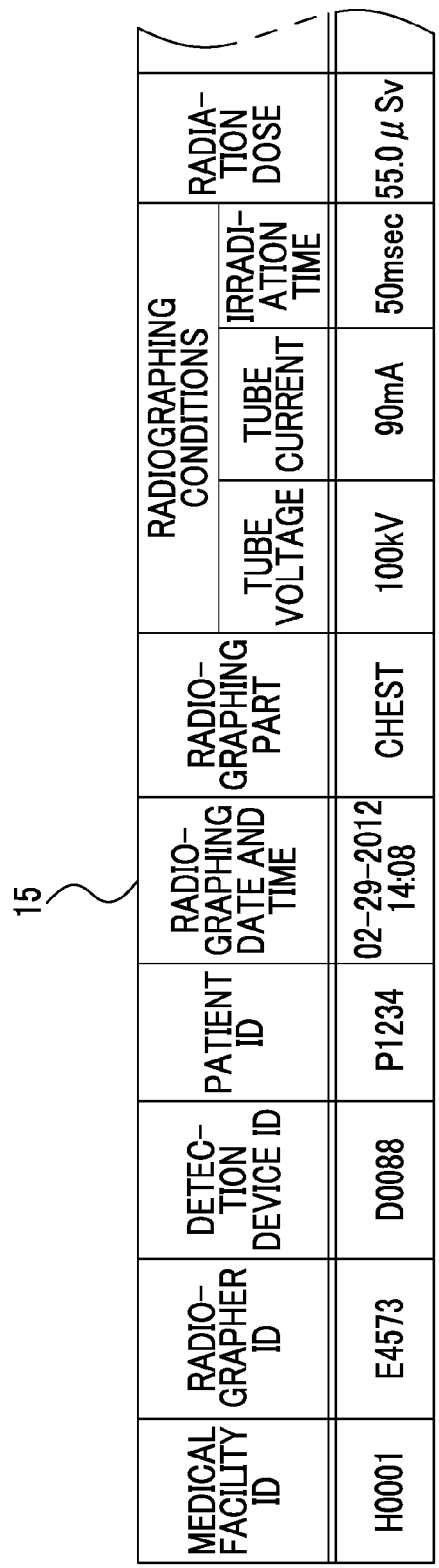
FIG. 2 is a diagram showing each item of radiographing information.

In FIG. 2, the radiographing information 15 includes items, such as an ID of the medical facility 11 in which the X-ray radiographing system 14 is placed, an ID of a radiographer in charge of radiographing, an ID of an X-ray image detection device used in radiographing, a patient ID, radiographing date and time, a radiographing part, radiographing conditions including a tube voltage and a tube current of an X-ray source and X-ray irradiation time, and a radiation dose detected by a dose detection sensor. These items are automatically collected into the client terminal 17 from various medical systems (for example, HIS (Hospital Information System) or RIS (Radiation Information System)) in the medical facility 11, which manage patient information or information related to the radiographing, or manually input.

The medical facility ID is issued from the data center 10 when the data center 10 and each medical facility 11 have a service contract. The radiographer ID and the patient ID are similarly issued from the data center 10. The medical facility ID, the radiographer ID, and the patient ID uniquely identify the medical facility 11, a radiographer, and a patient, respectively.

The detection device ID is information for uniquely identifying the X-ray image detection device, such as the type of the X-ray image detection device, a serial number, a part number, and a lot number. According to this detection device ID, the type of an X-ray image detection device, such as a CR cassette or a DR cassette, sensitivity to X-rays, whether the device is of a TFT type or a CMOS type or whether the device is of a direct conversion type or an indirect conversion type in the case of the DR cassette, which kind of material is used to form a scintillator, and the like can be checked. The information of the type of the X-ray image detection device may be added to the detection device ID, or may be added as a separate item from the detection device ID.

Each of the central server 13 and the client terminal 17 is configured by installing a control program, such as an operating system, or an application program, such as a server program or a client program, on a computer as a base, such as a computer for a server, a workstation, or a personal computer.

Figure 3:
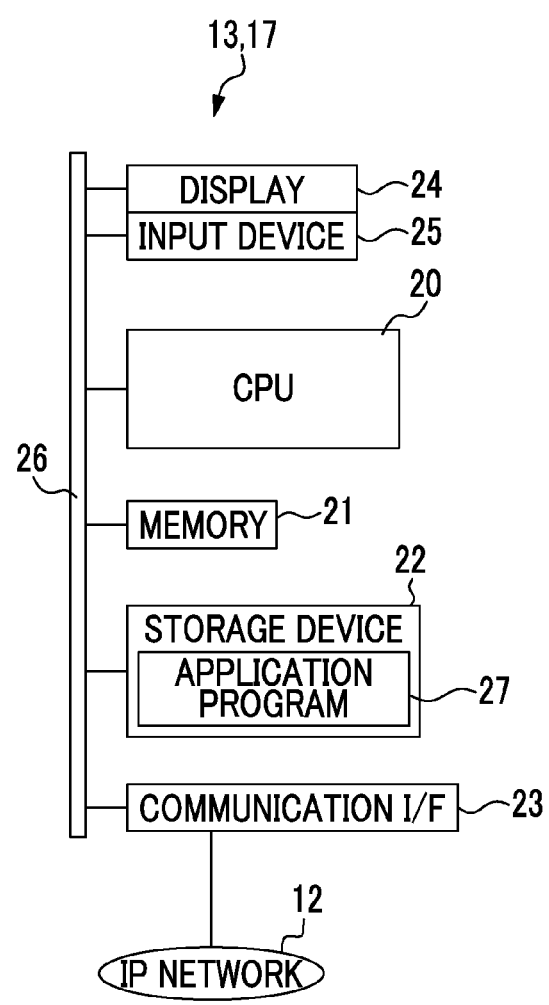
FIG. 3 is a block diagram showing a computer which forms each of a central server and a client terminal.

In FIG. 3, the basic configurations of computers that configure the central server 13 and the client terminal 17 are approximately the same, and each computer includes a CPU 20, a memory 21, a storage device 22, a communication I/F 23, a display 24, and an input device 25. These are connected to each other through a data bus 26.

The storage device 22 is an HDD (Hard Disk Drive) in the case of the client terminal 17 and a disk array, which is formed by connecting a plurality of HDDs, in the case of the central server 13, for example. A control program or an application program 27 is stored in the storage device 22. A server program to execute processing in response to the request from the client terminal 17 and send the processing result is installed in the central server 13 as the application program 27. A client program to perform processing for transmitting the radiographing information 15 or statistical data display processing is installed in the client terminal 17 as the application program 27.

The memory 21 is a work memory required when the CPU 20 executes processing. The CPU 20 performs overall control of each unit of the computer by loading the control program stored in the storage device 22 to the memory 21 and executing the processing according to the program. The communication I/F 23 is a network interface that performs data transmission control between the central server 13 and the client terminal 17 through the IP network 12. The input device 25 is a keyboard or a mouse or a touch panel united with the display 24. In addition, in the following explanation, for the sake of distinction, S is added after the numbers of the CPU 20, the storage device 22, and the like corresponding to the central server 13, and C is added after the numbers of the CPU 20, the storage device 22, and the like corresponding to the client terminal 17.

In FIG. 4, when a server program is started, the CPU 20S of the central server 13 functions as a storage processing unit 30, a search processing unit 31, a sorting unit 32, and a statistical data generation unit 33.

The storage processing unit 30 (an aspect of a storage processing unit) executes processing for storing the radiographing information 15 from the client terminal 17 of each medical facility 11, which has been received through the communication I/F 23S, in the storage device 22S (an aspect of a storage unit). The search processing unit 31 (an aspect of a search unit) searches for and extracts the radiographing information 15 matched with a designated radiographing part, among all items of the radiographing information 15 of the medical facility 11 having the radiographing information 15 matched with a designated detection device ID, in response to the transmission request of the statistical data 16 from the client terminal 17 to which the information of a radiographing part and the detection device ID to designate an X-ray image detection device, which are targets of the statistical data 16, is given. The search processing unit 31 transmits the extracted radiographing information 15 to the sorting unit 32.

Figure 5A:
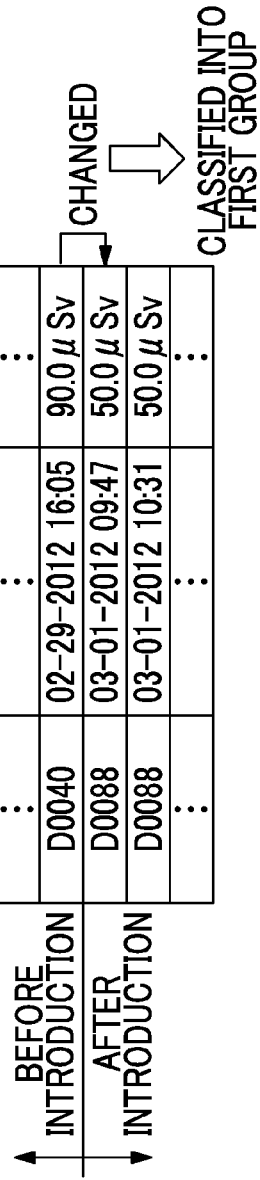

The sorting unit 32 (an aspect of an analysis unit) sorts the radiographing information 15 in chronological order of radiographing date and time for each medical facility 11 with reference to the items of the medical facility ID and radiographing date and time of the radiographing information 15 received from the search processing unit 31 and groups the radiographing information 15 for each medical facility 11. As a result, the radiographing information 15 is listed as shown in FIGS. 5A and 5B. In this example, D0088 and a chest are designated as the detection device ID and the radiographing part, respectively, in the transmission request, and all items of the radiographing information 15, in which the radiographing part is a chest, of the medical facility A and B having the radiographing information 15 of the detection device ID are listed. In addition, items, such as a patient ID and radiographing conditions, are omitted. Since the radiographing information 15 matched with a designated radiographing part, among all items of the radiographing information 15 of the medical facility 11 having the radiographing information 15 matched with a designated detection device ID, is searched for and extracted by the search processing unit 31, the radiographing information 15 (D0040 or D0072) before the X-ray image detection device of the designated detection device ID was introduced is also listed. When a new X-ray image detection device of the designated detection device ID is further purchased, the radiographing information 15 after purchasing is also listed as shown as D0090 of the medical facility B.

The sorting unit 32 analyzes the list of the radiographing information 15 of each medical facility 11, and assesses states before and after the introduction of the X-ray image detection device of the designated detection device ID with reference to the detection device ID. In addition, the medical facilities 11 are classified into the medical facility 11 (first group), in which the radiation dose after the X-ray image detection device of the designated detection device ID is introduced has changed from that before the introduction, and the medical facility 11 (second group), in which the radiation dose after the X-ray image detection device of the designated detection device ID is introduced has not changed.

This will be specifically described in the example of FIGS. 5A and 5B. In the medical facility A, the detection device ID has changed from D0040 to D0088 at radiographing date and time Feb. 29, 2012 16:05 and Mar. 1, 2012 9:47. Accordingly, it can be determined that the radiographing information before Feb. 29, 2012 16:05 is the radiographing information 15 before the X-ray image detection device of D0088 was introduced and the radiographing information from Mar. 1, 2012 9:47 is the radiographing information 15 after the X-ray image detection device of D0088 was introduced. Similarly, also in the case of the medical facility B, it can be determined that the radiographing information before Feb. 29, 2012 14:08 is the radiographing information 15 before the X-ray image detection device of D0088 was introduced and the radiographing information from Feb. 29, 2012 16:22 is the radiographing information 15 after the X-ray image detection device of D0088 was introduced.

In the medical facility A, the radiation dose after the introduction of the X-ray image detection device of D0088 is lower than that before the introduction. That is, the radiation dose after the introduction has changed from that before. In contrast, in the medical facility B, the radiation dose has not changed even after the introduction of the X-ray image detection device of D0088, compared with that before the introduction. Therefore, the medical facility A is classified into the first group, and the medical facility B is classified into the second group.

The sorting unit 32 transmits the result of the classification of the medical facilities 11 and the information of the radiation dose of each medical facility 11 after the X-ray image detection device of the designated detection device ID is introduced (50 µSv in the case of the medical facility A, and 65 µSv in the case of the medical facility B) to the statistical data generation unit 33.

In addition, in order to simplify explanation herein, the radiation dose when the detection device ID is D0040 in the medical facility A is 90 µSv, and the radiation dose when the detection device ID is D0088 in the medical facility A is 50 µSv. That is, there is no change in the radiation dose. In practice, however, there are some variations. For this reason, when classifying groups, the sorting unit 32 may calculate the average value of the radiation doses before and after introduction, and perform classification into the first group since there is a change when the difference between the average values exceeds a predetermined range and perform classification into the second group since there is no change when the difference between the average values falls within the predetermined range. In this case, a predetermined range is appropriately set in consideration of a radiographing part, magnitude of the variation, and the like.

When a long time has not passed from the introduction of a new X-ray image detection device, the radiographer undergoes trial and error in optimizing the radiographing conditions to realize low-dose radiographing. Accordingly, there is a possibility that the radiation dose will change significantly. For this reason, it is preferable that the medical facility 11, in which a predetermined period, for example, a week or a month has not passed from the introduction of a new X-ray image detection device, be not classified into a group. In addition, also when performing classification into groups, it is preferable to determine whether or not there is a change in the radiation dose after introduction from that before based on the radiation dose after the passage of a predetermined period rather than the radiation dose immediately after the introduction of a new X-ray image detection device.

In addition, a case may also be considered in which radiographing is performed using an existing X-ray image detection device even after a new X-ray image detection device is introduced. In this case, states before and after the introduction of the X-ray image detection device are assessed with a point in time when the detection device ID has first changed as a reference.

Figure 6A:
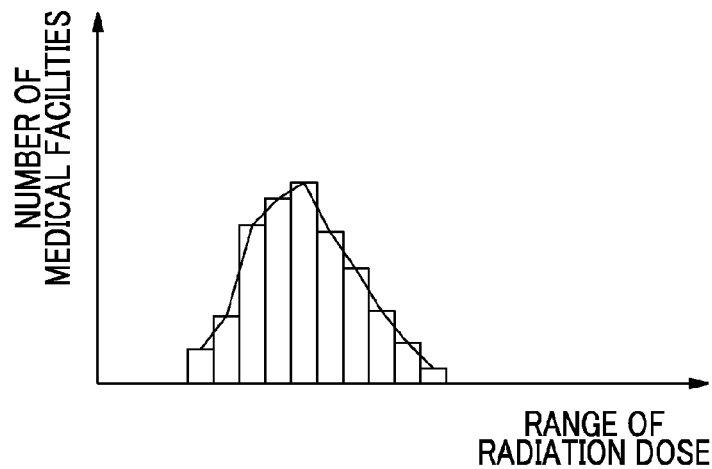
FIGS. 6A and 6B are graphs showing first and second statistical data that are separately generated for a first group, in which the radiation dose has changed after introduction of an X-ray image detection device from that before, and a second group, in which the radiation dose after the introduction has not changed.
Figure 6B:
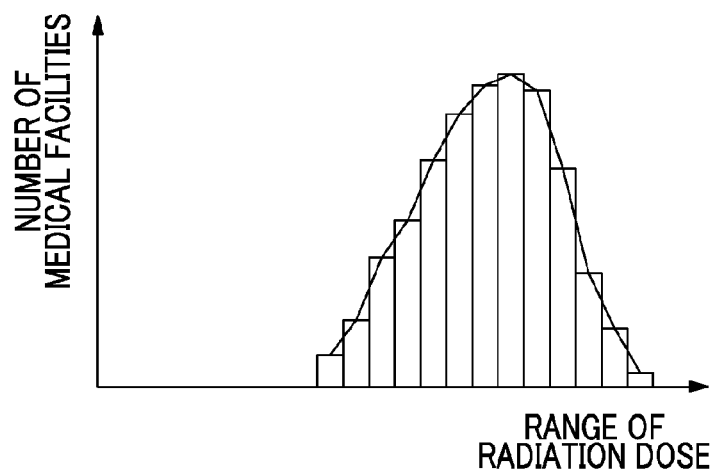

The statistical data generation unit 33 (an aspect of a statistical data generation unit) generates first and second statistical data for first and second groups based on the classification result and the dose information from the sorting unit 32. Specifically, histograms shown in FIGS. 6A and 6B are generated as statistical data. In these histograms, the range of radiation dose, such as 0 to 5 µSv and 6 to 10 µSv, is set as the class on the horizontal axis, and the number of medical facilities is set as the frequency on the vertical axis. FIG. 6A is a histogram (first statistical data) of the medical facilities 11 in which the radiation dose has changed after the introduction of an X-ray image detection device from that before, that is, a histogram of a first group. In contrast, FIG. 6B is a histogram (second statistical data) of a second group in which the radiation dose has not changed after the introduction from that before.

Here, it is assumed that a newly introduced X-ray image detection device has higher X-ray detection sensitivity than an X-ray image detection device before the new X-ray image detection device is introduced and accordingly an X-ray image with the image quality, which is not different from that before the introduction of the new X-ray image detection device, can be acquired even if the radiation dose is suppressed compared with that before the introduction. Since it is thought that there is no user who purchases an X-ray image detection device with poor performance when purchasing a new X-ray image detection device, there would be no mistake even if the X-ray image detection device that is newly introduced as described above is said to have higher X-ray detection sensitivity than before.

In the medical facility 11 actively engaged in low-dose radiographing, efforts to reduce the radiation dose are made by changing the radiographing conditions after the introduction of an X-ray image detection device, as in the medical facility A shown in FIG. 5A. Since the first group is a collection of such medical facilities 11, the peak of a histogram is located toward the low dose end. In contrast, the second group does not know how to reduce the radiation dose, or the setting of the optimal radiographing conditions is difficult even if the second group knows how to reduce the radiation dose. Therefore, as in the medical facility B shown in FIG. 5B, since the second group is a collection of medical facilities 11 where low-dose radiographing cannot be achieved, the peak of a histogram is located toward the high dose end compared with the first group.

Figure 7:
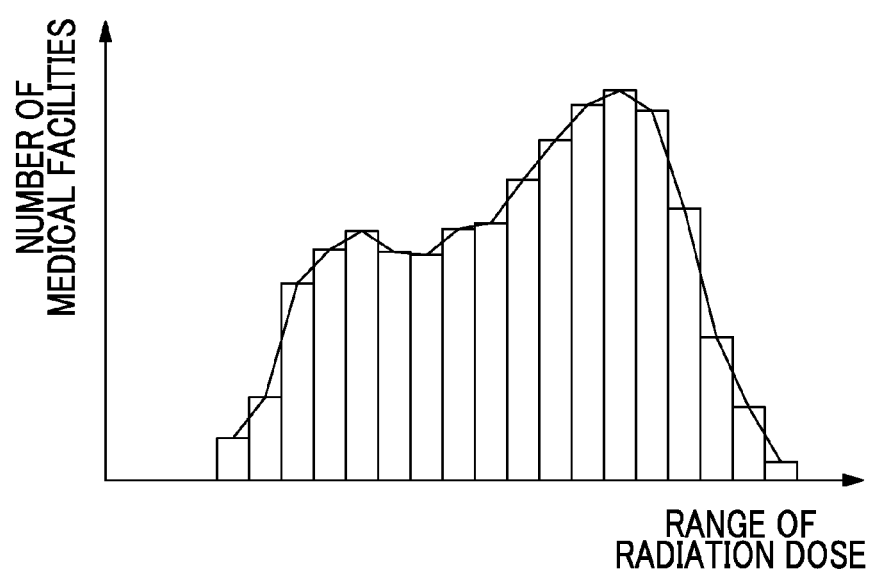
FIG. 7 is a graph showing the statistical data generated without classification into first and second groups.

A histogram shown in FIG. 7 is obtained by adding the histograms shown in FIGS. 6A and 6B without classification into the first and second groups. From this histogram, an overall image of the radiation dose distribution can be seen. However, it is difficult to know how much the radiation dose can be reduced by introducing an X-ray image detection device. In addition, when the high dose side looks rather dominant as in this example, the histogram may mislead the viewer into believing that low-dose radiographing cannot be achieved even if the X-ray image detection device is introduced. In contrast, in this example, it is possible to specify that a transition to low-dose radiographing is possible depending on radiographing conditions by classifying medical facilities into the first and second groups and generating a histogram for each of the groups.

The statistical data generation unit 33 transmits the generated first and second statistical data to the communication I/F 23S. The communication I/F 23S transmits the first and second statistical data to the client terminal 17 that has transmitted a transmission request.

Figure 8:
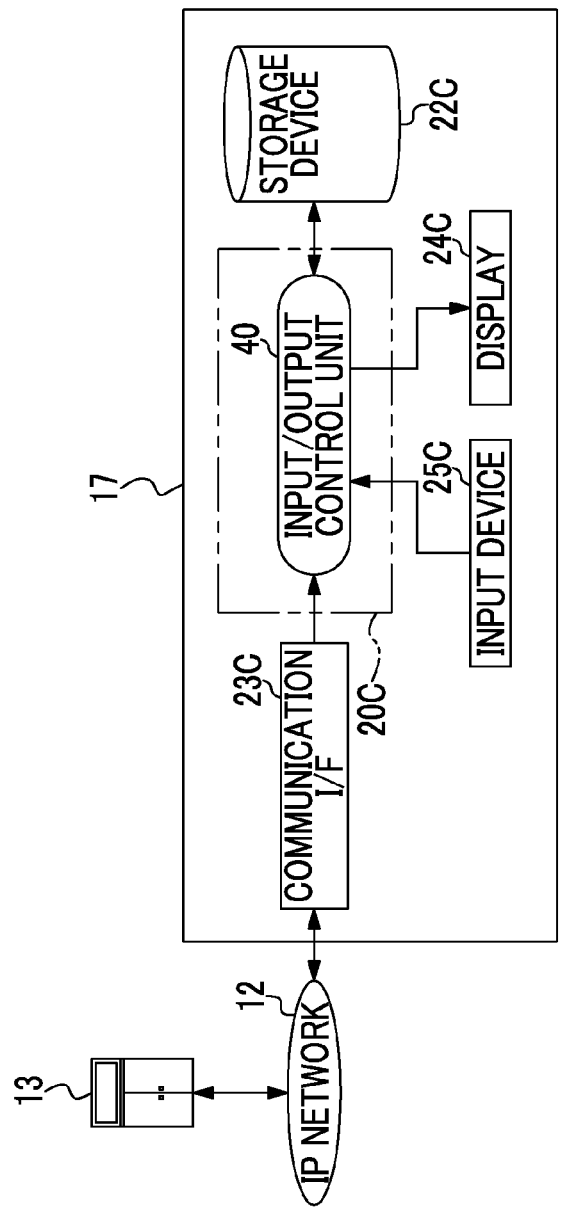
FIG. 8 is a block diagram showing the internal configuration of a client terminal.

In FIG. 8, when a client program starts, the CPU 20C of the client terminal 17 functions as an input/output control unit 40. The input/output control unit 40 reads screen data according to the operation of the input device 25C from the storage device 22C and outputs various operation screens to the display 24C based on the read screen data. The input/output control unit 40 receives the input of an operation instruction from the input device 25C through a GUI disposed on the operation screen.

Figure 9:
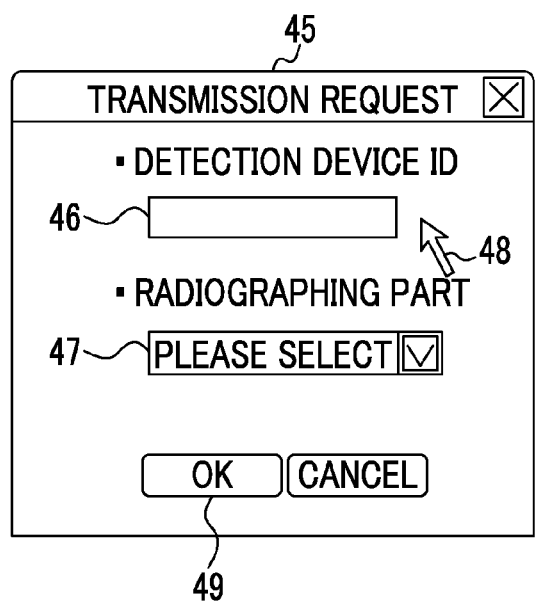
FIG. 9 is a diagram showing a transmission request window.

The input/output control unit 40 displays a transmission request window 45 shown in FIG. 9 on the display 24C when the operator of the client terminal 17 requests the central server 13 to transmit the statistical data 16. An input box 46 for inputting a detection device ID and a pull-down menu 47 for selecting a radiographing part are displayed as a GUI in the transmission request window 45. The operator performs keyboard input of a detection device ID, for which the statistical data 16 is needed, by moving a cursor 48 of a mouse to the input box 46, selects a desired radiographing part by clicking the pull-down menu 47 with the cursor 48, and then clicks an OK button 49 with the cursor 48. When the OK button 49 is clicked, the input/output control unit 40 transmits the information of the detection device ID input to the input box 46 and the radiographing part selected in the pull-down menu 47, as a transmission request, from the communication I/F 23C to the central server 13.

When the statistical data 16 from the central server 13 is received through the communication I/F 23C, the input/output control unit 40 displays a statistical data display window 55 shown in FIG. 10 on the display 24C. In the statistical data display window 55, first statistical data under the heading "group successful in low-dose radiographing" in the meaning of the first group and second statistical data under the heading "group not successful in low-dose radiographing" in the meaning of the second group are displayed side by side in addition to the detection device ID and the radiographing part designated in the transmission request. In addition, it is possible to display how much radiation dose is used to perform radiographing in the medical facility 11 in which there is the client terminal 17 that has transmitted a transmission request. For example, the arrow and "Your Position" indicated by reference numeral 56 may be displayed.

A display switching button 57 is provided in the statistical data display window 55. When the display switching button 57 is clicked with the cursor 48, the input/output control unit 40 changes the display of the statistical data 16 to the parallel display of the first and second statistical data, which is shown in the drawing, and display of each item of the statistical data. Only the first statistical data may be separately displayed without separate display of the second statistical data. In addition, the first and second statistical data items may be displayed so as to overlap each other on one graph, or the result obtained by adding the first and second statistical data items may be displayed as shown in FIG. 7.

Hereinafter, the operation based on the above-described configuration will be described with reference to the flow chart shown in FIG. 11. First, in the medical facility 11, X-ray radiographing is performed using the X-ray radiographing system 14 (S10 (step 10)). The radiographing information 15 at this time is transmitted and received between the communication I/F 23C of the client terminal 17 and the communication I/F 23S of the central server 13 (S11 and S20). In the central server 13, the radiographing information 15 received through the communication I/F 23S is stored in the storage device 22S by the storage processing unit 30 (S21).

A transmission request of the statistical data 16 is made through the transmission request window 45 in the client terminal 17, and this transmission request is transmitted and received between the communication I/F 23C of the client terminal 17 and the communication I/F 23S of the central server 13 (S12 and S22).

In the central server 13, the radiographing information 15 matched with a designated radiographing part is searched for and extracted among all items of the radiographing information 15 of the medical facility 11 having the radiographing information 15 matched with a detection device ID designated in the transmission request (S23). Then, the sorting unit 32 sorts the radiographing information 15 in chronological order of radiographing date and time for each medical facility 11. As a result, the radiographing information 15 is listed. Then, the medical facilities 11 are classified into a first group, in which the radiation dose after the X-ray image detection device of the detection device ID designated in the transmission request is introduced has changed from that before the introduction, and a second group, in which the radiation dose after the X-ray image detection device of the designated detection device ID is introduced has not changed (S24). Based on this classification result and the information of the radiation dose after the X-ray image detection device of the detection device ID designated in the transmission request is introduced, the statistical data generation unit 33 generates first and second statistical data for the first and second groups (S25). This data is transmitted and received between the communication I/F 23S and the communication I/F 23C (S13 and S26). In the client terminal 17, the input/output control unit 40 displays the statistical data display window 55 on the display 24C based on the first and second statistical data received through the communication I/F 23C (S14).

The operator of the client terminal 17 views the statistical data display window 55 on the display 24C. The content of the statistical data display window 55 may be printed by a printer, or may be stored in the storage device 22C. In this manner, the statistical data may be used as reference material for a change to the radiographing conditions for low-dose radiographing, or may be used as material for informed consent of a patient.

As described above, according to the present invention, the central server 13 generates statistical data separately for the first group in which the radiation dose after the X-ray image detection device is introduced has changed and the second group in which the radiation dose after the X-ray image detection device is introduced has not changed, and transmits the statistical data to the client terminal 17 to display the statistical data. Therefore, the effect of a reduction in the radiation dose due to the introduction of a new X-ray image detection device with high X-ray detection sensitivity can be clearly seen visually.

Since the medical facility 11 of the first group can appeal to the patient that they are actively engaged in low-dose radiographing, a feeling of safety can be given to the patient. The medical facility 11 of the second group can be encouraged to make an effort for low-dose radiographing. In addition, if a salesman carries a printout of statistical data and has a business talk with a person in charge of purchasing in the medical facility 11, who is wondering if a new X-ray image detection device needs to be introduced, while showing the person the printout, it becomes a great incentive to purchase the X-ray image detection device. This helps to promote sales.

In the above embodiment, the X-ray radiographing information management system 2 configured to include the data center 10 and a plurality of medical facilities 11 has been illustrated. However, these may also be provided in one medical facility as an X-ray radiographing information management system 60 shown in FIG. 12.

Figure 12:
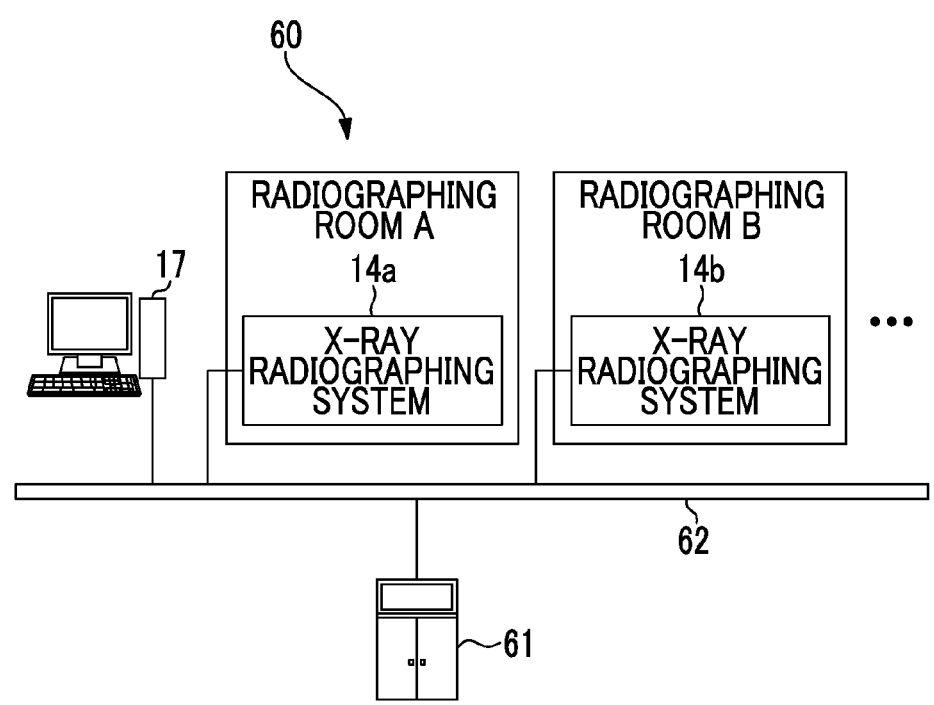
FIG. 12 is a diagram showing an example where an X-ray radiographing information management system is built in a single medical facility.

In FIG. 12, the X-ray radiographing information management system 60 has a configuration in which a plurality of X-ray radiographing systems 14a, 14b, . . . placed in a plurality of radiographing rooms A, B, . . . of the medical facility, a client terminal 17, and an X-ray radiographing information management apparatus 61 are connected to each other through a LAN 62 provided in the medical facility. The X-ray radiographing information management apparatus 61 corresponds to the central server 13 in the embodiment described above.

In this case, a radiographing room ID is added to the items of radiographing information instead of the medical facility ID, and the unit of groups classified by the sorting unit is assumed to be a radiographing room. Alternatively, groups are classified in units of a radiographer belonging to the medical facility. The achievement situation of low-dose radiographing can be checked in units of a radiographing room or a radiographer. In addition, in the case of a single medical facility, the number of radiographing rooms or the number of radiographers is small. For this reason, if the statistical data is expressed with a histogram as in the embodiment described above, it looks poor. Accordingly, the number of first and second groups may be expressed using a table, or the number of radiographing rooms or the number of radiographers may be listed for each separate group.

In the X-ray radiographing information management system 2 of the embodiment described above, as a unit of the groups classified by the sorting unit, a radiographer may be adopted instead of the medical facility. A GUI for selecting the unit of the classified group is added to the transmission request window, and the selected information is transmitted to the central server 13 as a transmission request. Radiographing information matched with a designated radiographing part, among all items of radiographing information of a radiographer having the radiographing information 15 matched with a detection device ID designated in the transmission request, is searched for and extracted by the search processing unit 31. The procedure of subsequent sorting and statistical data generation is the same as that in the embodiment described above.

Although a single X-ray image detection device is targeted in the above embodiment, detection device IDs of a plurality of X-ray image detection devices may be designated in the transmission request, and statistical data regarding a plurality of X-ray image detection devices may be acquired by a single transmission request. In this case, if the statistical data of the plurality of X-ray image detection devices is displayed side by side or so as to overlap each other in the statistical data display window so that the statistical data can be compared with each other, the superiority of the X-ray image detection devices is self-explanatory.

In the above embodiment, the radiation dose detected by the dose detection sensor of the X-ray radiographing system 14 has been described as an example. However, instead of the radiation dose itself, an amount equivalent to the radiation dose may be used. For example, a tube current irradiation time product (mAs value), which is set in the X-ray source at the time of X-ray irradiation, or a reading sensitivity value (S value), which is obtained by analyzing an X-ray image using a histogram, may also be used. The mAs value may be calculated from the tube current and irradiation time of the radiographing conditions. When the S value is used, radiographing information and X-ray image data are transmitted between the client terminal and the central server or the X-ray radiographing information management apparatus, and the X-ray image data is stored in the storage device of the central server or the X-ray radiographing information management apparatus so as to be associated with the radiographing information. In addition, an image analysis unit for calculating the S value from the X-ray image data is built in the CPU of the central server or the X-ray radiographing information management apparatus. If only the X-ray image data is present, the S value can be calculated even if there are no radiographing conditions. Accordingly, the S value is preferably used when the radiographing conditions are not included in the radiographing information. However, since the definition of the S value changes slightly depending on the manufacturer, the S value is corrected and standardized to become a uniform value irrespective of the manufacturer.

The assessment of the states before and after the introduction of a new X-ray image detection device is not limited to the method of assessing the switching of the detection device ID in the embodiment described above. An operator may manually input in a client terminal that a new X-ray image detection device has been introduced, and the information may be transmitted to a central server or an X-ray radiographing information management apparatus. Receiving date and time of the information may be stored for each medical facility in the central server or the X-ray radiographing information management apparatus, and before and after the receiving date and time may be determined to be before and after the introduction of the new X-ray image detection device.

In the embodiment described above, the radiographing information searched for and extracted by the search processing unit is sorted and listed by the sorting unit. However, the storage processing unit may be made to have a function of the sorting unit, and the radiographing information may be collectively stored in a storage device in time series in advance in units of a group, for example, for each medical facility.

In the embodiment described above, statistical data of both the first and second groups is generated and displayed. However, as material for realizing low-dose radiographing, statistical data of the first group is highly useful. Accordingly, only the statistical data of at least the first group is preferably generated.

In the embodiment described above, displaying the statistical data visually has been described. However, optimal radiographing conditions may be simply presented from the statistical data of the first group instead of visual display. For example, radiographing conditions of the place where the average of the radiographing conditions of the first group or the frequency of the histogram of the first group is greatest may be presented. The definition of the optimal radiographing conditions may be considered in various ways without being limited to the above examples, such as the average.

The function of the sorting unit or the statistical data generation unit may be added to the client terminal. In this case, search results of the search processing unit or classification results of the sorting unit are transmitted from the central server or the X-ray radiographing information management apparatus to the client terminal. In addition, a client terminal to transmit the radiographing information and a client terminal to receive the statistical data may be separate terminals. There may be a plurality of client terminals. In short, units of the present invention may be separately provided in a plurality of apparatuses. Alternatively, as in the embodiment described above, the client terminal may have a function of only the display unit, and the central server or the X-ray radiographing information management apparatus may have functions of other units.

Medical facilities, radiographers, or radiographing conditions of a radiographing room, which realize low-dose radiographing, may be viewed through the client terminal 17. For example, a link to medical facilities, radiographers, or radiographing conditions of a radiographing room, which realize low-dose radiographing, is set in the statistical data display window 55, and the radiographing conditions are displayed on the display 24C when the link is clicked. In this case, the radiographing conditions are preferably displayed so as to be able to be compared with the current radiographing conditions.

In addition, the present invention may also be applied to the radiographing information management of a radiographing system that uses other radiations, such as y-rays, without being limited to the X-rays.

What is claimed is:

1. A radiographing information management system comprising:
    a storage processing unit that stores radiographing information in a storage unit;
    a search unit that searches for desired radiographing information from the storage unit;
    an analysis unit that analyzes the radiographing information; and
    a statistical data generation unit that generates statistical data based on the radiographing information analyzed by the analysis unit,
    wherein the radiographing information includes at least source identification information indicating a source of the radiographing information, detection device identification information indicating a radiological image detection device used in radiographing, and information regarding a radiation dose,
    the search unit searches for, from the radiographing information, radiographing information when performing radiographing using a designated radiological image detection device,
    the analysis unit groups the radiographing information for each item of the source identification information, assesses states before and after introduction of the radiological image detection device based on detection device identification information or information regarding switching of a type of a radiological image detection device, among the grouped radiographing information items, and performs classification into a first group in which a difference between information regarding a radiation dose before the radiological image detection device is introduced and information regarding a radiation dose after the radiological image detection device is introduced exceeds a predetermined range, and a second group in which the difference falls within the predetermined range, and
    the statistical data generation unit generates statistical data of at least the first group.

2. The radiographing information management system according to claim 1, further comprising:
    a display unit that displays statistical data generated by the statistical data generation unit.

3. The radiographing information management system according to claim 2,
    wherein, when the statistical data generation unit generates statistical data of the first and second groups, the display unit displays the statistical data of the first and second groups so as to be compared with each other, or displays only the statistical data of the first group.

4. The radiographing information management system according to claim 1,
    wherein the statistical data generation unit generates a histogram, in which a vertical axis indicates the number of groups and a horizontal axis indicates a range of a radiation dose or an equivalent amount equivalent to the radiation dose, as statistical data.

5. The radiographing information management system according to claim 1,
    wherein the statistical data generation unit calculates optimal radiographing conditions from the statistical data of the first group.

6. The radiographing information management system according to claim 1,
wherein the search unit performs searching in response to a transmission request of statistical data including detection device identification information to be searched for.

7. The radiographing information management system according to claim 6,
wherein the radiographing information includes information of a radiographing part,
the transmission request includes information of a radiographing part, and
the search unit searches for radiographing information, which is matched with a radiographing part designated in the transmission request, among radiographing information having detection device identification information designated in the transmission request.

8. The radiographing information management system according to claim 1,
wherein the analysis unit excludes a group of radiographing information, for which a predetermined period has not passed since the radiological image detection device has been introduced, from objects to be classified.

9. The radiographing information management system according to claim 1,
wherein the radiographing information includes, as the source identification information, any one of a medical facility in which a radiographing system is placed, a radiographer in charge of radiographing, and a radiographing room where radiographing is performed, and
the analysis unit groups radiographing information based on any one of the medical facility, the radiographer, and the radiographing room.

10. The radiographing information management system according to claim 1,
wherein information regarding switching of a type of the radiological image detection device is date and time when the radiological image detection device is newly introduced.

11. The radiographing information management system according to claim 1,
wherein the information regarding a radiation dose is any one of the radiation dose itself, a tube current irradiation time product, and a reading sensitivity value obtained by histogram analyzing of a radiological image.

12. A radiographing information management method comprising:
a storage processing step of storing radiographing information in a storage unit using a storage processing unit;
a search step of searching for desired radiographing information from the storage unit using a search unit;
an analysis step of analyzing the radiographing information; and
a statistical data generation step of generating statistical data based on the radiographing information analyzed in the analysis step using a statistical data generation unit,
wherein the radiographing information includes at least source identification information indicating a source of the radiographing information, detection device identification information indicating a radiological image detection device used in radiographing, and information regarding a radiation dose,
in the search step, radiographing information when performing radiographing using a designated radiological image detection device is searched for from the radiographing information,
in the analysis step, the radiographing information is grouped for each item of the source identification information, states before and after introduction of the radiological image detection device are assessed based on detection device identification information or information regarding switching of a type of a radiological image detection device among the grouped radiographing information items, and classification into a first group in which a difference between information regarding a radiation dose before the radiological image detection device is introduced and information regarding a radiation dose after the radiological image detection device is introduced exceeds a predetermined range and a second group in which the difference falls within the predetermined range is performed, and
in the statistical data generation step, statistical data of at least the first group is generated.

13. A non-transitory computer-readable recording medium that records a radiographing information management program causing a computer to realize:
a storage processing function of storing radiographing information in a storage unit;
a search function of searching for desired radiographing information from the storage unit;
an analysis function of analyzing the radiographing information; and
a statistical data generation function of generating statistical data based on the radiographing information analyzed by the analysis function,
wherein the radiographing information includes at least source identification information indicating a source of the radiographing information, detection device identification information indicating a radiological image detection device used in radiographing, and information regarding a radiation dose,
using the search function, radiographing information when performing radiographing using a designated radiological image detection device is searched for from the radiographing information,
using the analysis function, the radiographing information is grouped for each item of the source identification information, states before and after introduction of the radiological image detection device are assessed based on detection device identification information or information regarding switching of a type of a radiological image detection device among the grouped radiographing information items, and classification into a first group in which a difference between information regarding a radiation dose before the radiological image detection device is introduced and information regarding a radiation dose after the radiological image detection device is introduced exceeds a predetermined range and a second group in which the difference falls within the predetermined range is performed, and
using the statistical data generation function, statistical data of at least the first group is generated.

* * * * *